(12) United States Patent
Hug et al.

(10) Patent No.: US 7,517,347 B2
(45) Date of Patent: Apr. 14, 2009

(54) ELECTROSURGICAL INSTRUMENT FOR AN ENDOSCOPE OR A CATHETER

(75) Inventors: Bernhard Hug, Frelburg (DE); Herbert Maslanka, Im Jungen Seigle 4, 78532 Tuttlingen (DE)

(73) Assignees: KLS Martin GmbH & Co. KG, Umkirch (DE); Herbert Maslanka, Tuttlingen (DE)

(*) Notice: Subject to any disclaimer, the term of this patent is extended or adjusted under 35 U.S.C. 154(b) by 693 days.

(21) Appl. No.: 10/559,523

(22) PCT Filed: Jun. 16, 2004

(86) PCT No.: PCT/EP2004/006488

§ 371 (c)(1),
(2), (4) Date: Dec. 6, 2005

(87) PCT Pub. No.: WO2004/110294

PCT Pub. Date: Dec. 23, 2004

(65) Prior Publication Data

US 2007/0034211 A1    Feb. 15, 2007

(30) Foreign Application Priority Data

Jun. 17, 2003    (DE) ............................... 103 27 237

(51) Int. Cl.
*A61B 18/18* (2006.01)

(52) U.S. Cl. .............................. 606/45; 606/41; 606/37; 606/46; 607/101; 604/113

(58) Field of Classification Search ...................... 604/8, 604/33, 35, 101, 113; 607/101, 102, 122, 607/156; 606/41–50, 32, 34, 38, 47, 110
See application file for complete search history.

(56) References Cited

U.S. PATENT DOCUMENTS 3,920,021 A * 11/1975 Hiltebrandt ................... 606/50

(Continued)

FOREIGN PATENT DOCUMENTS

DE    195 35 811 C1    4/1997

(Continued)

OTHER PUBLICATIONS

International Preliminary Report on Patentability issued May 1, 2006.

(Continued)

*Primary Examiner*—Terrell L McKinnon
*Assistant Examiner*—Amanda Scott
(74) *Attorney, Agent, or Firm*—Scott D. Wofsy; Edwards Angell Palmer & Dodge LLP

(57) ABSTRACT

The invention relates to an electrosurgical instrument (5) for an endoscope or a catheter, which can be operated by means of a high-frequency current, contact electrosurgical treatment and non-contact plasma coagulation in an ionisable gas. A stationary electrode (33) is arranged on the distal end of a guiding tube (7) that can be introduced into the instrument channel (1) of an endoscope catheter (3), and when the electrosurgical electrode for the contact treatment is in the retracted position in the guiding tube (7), the stationary electrode is connected to the electrosurgical electrode (11) by means of a contact element (37). The retracted position of the electrode (11) can, but not necessarily, be maintained by an abutment (21) of a handling device (13) and/or by a suitable arrangement and measurement of the contact element (37). The retracted position of the electrode (11) does not need to be optically controlled.

22 Claims, 2 Drawing Sheets

U.S. PATENT DOCUMENTS

| Patent No. | | | Date | Inventor | Class |
|---|---|---|---|---|---|
| 4,311,145 | A | * | 1/1982 | Esty et al. | 606/42 |
| 4,781,175 | A | * | 11/1988 | McGreevy et al. | 606/40 |
| 5,098,430 | A | * | 3/1992 | Fleenor | 606/42 |
| 5,197,963 | A | * | 3/1993 | Parins | 606/46 |
| 5,197,964 | A | * | 3/1993 | Parins | 606/48 |
| 5,207,675 | A | * | 5/1993 | Canady | 606/40 |
| 5,217,457 | A | * | 6/1993 | Delahuerga et al. | 606/42 |
| 5,244,462 | A | * | 9/1993 | Delahuerga et al. | 606/42 |
| 5,269,780 | A | * | 12/1993 | Roos | 606/42 |
| 5,290,286 | A | * | 3/1994 | Parins | 606/50 |
| 5,306,238 | A | * | 4/1994 | Fleenor | 606/42 |
| 5,437,665 | A | * | 8/1995 | Munro | 606/47 |
| 5,441,499 | A | * | 8/1995 | Fritzsch | 606/45 |
| 5,514,130 | A | * | 5/1996 | Baker | 606/41 |
| 5,720,745 | A | * | 2/1998 | Farin et al. | 606/49 |
| 5,733,283 | A | * | 3/1998 | Malis et al. | 606/48 |
| 5,766,167 | A | * | 6/1998 | Eggers et al. | 606/46 |
| 5,830,214 | A | * | 11/1998 | Flom et al. | 606/41 |
| 5,849,011 | A | * | 12/1998 | Jones et al. | 606/47 |
| 5,891,141 | A | * | 4/1999 | Rydell | 606/45 |
| 5,897,554 | A | * | 4/1999 | Chia et al. | 606/41 |
| 5,902,300 | A | * | 5/1999 | Hahnen et al. | 606/46 |
| 5,976,129 | A | * | 11/1999 | Desai | 606/40 |
| 6,039,736 | A | * | 3/2000 | Platt, Jr. | 606/49 |
| 6,063,084 | A | * | 5/2000 | Farin | 606/49 |
| 6,090,105 | A | * | 7/2000 | Zepeda et al. | 606/41 |
| 6,190,384 | B1 | * | 2/2001 | Ouchi | 606/47 |
| 6,238,392 | B1 | * | 5/2001 | Long | 606/41 |
| 6,280,441 | B1 | * | 8/2001 | Ryan | 606/45 |
| 6,287,304 | B1 | * | 9/2001 | Eggers et al. | 606/37 |
| 6,391,027 | B1 | * | 5/2002 | Farin et al. | 606/45 |
| 6,423,060 | B1 | * | 7/2002 | Ouchi | 606/41 |
| 6,458,125 | B1 | * | 10/2002 | Cosmescu | 606/42 |
| 6,471,700 | B1 | * | 10/2002 | Burbank et al. | 606/45 |
| 6,497,704 | B2 | * | 12/2002 | Ein-Gal | 606/41 |
| 6,514,248 | B1 | * | 2/2003 | Eggers et al. | 606/41 |
| 6,558,383 | B2 | * | 5/2003 | Cunningham et al. | 606/41 |
| 6,602,249 | B1 | * | 8/2003 | Stoddard et al. | 606/45 |
| 6,666,865 | B2 | * | 12/2003 | Platt | 606/49 |
| 6,730,081 | B1 | * | 5/2004 | Desai | 606/40 |
| 6,837,888 | B2 | * | 1/2005 | Ciarrocca et al. | 606/41 |
| 6,899,712 | B2 | * | 5/2005 | Moutafis et al. | 606/49 |
| 2002/0022838 | A1 | | 2/2002 | Cunningham et al. | |
| 2002/0111623 | A1 | * | 8/2002 | Durgin et al. | 606/45 |
| 2003/0114850 | A1 | * | 6/2003 | McClurken et al. | 606/50 |

FOREIGN PATENT DOCUMENTS

| | | |
|---|---|---|
| DE | 91 17 299 U1 | 3/2000 |
| DE | 198 58 375 A1 | 7/2000 |
| DE | 19858375 A1 * | 7/2000 |
| EP | 0 765 638 A1 | 4/1997 |

OTHER PUBLICATIONS

International Preliminary Report on Patentability dated Dec. 19, 2005.

German Search Report dated May 26, 2004.

* cited by examiner

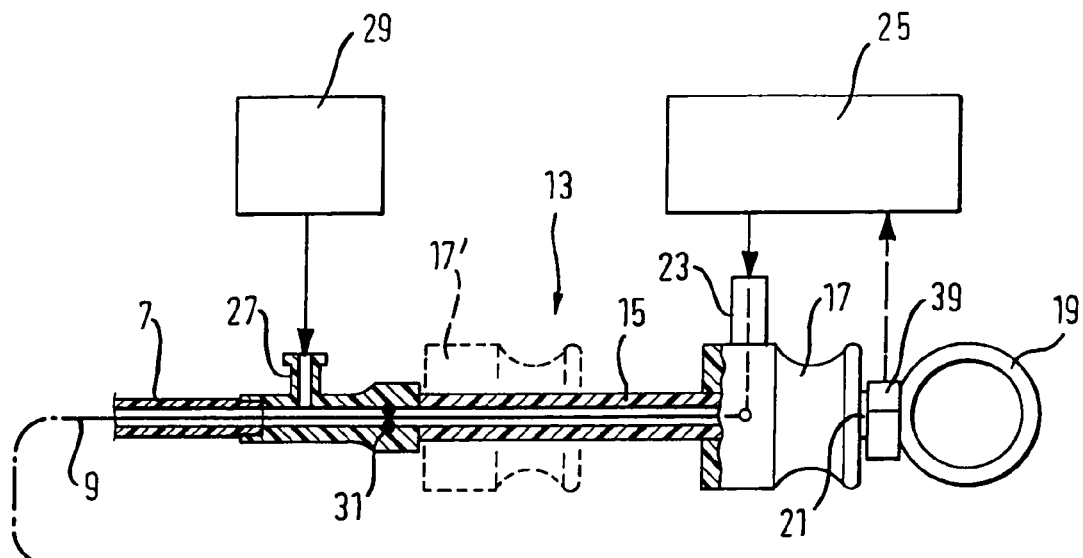
Fig. 1
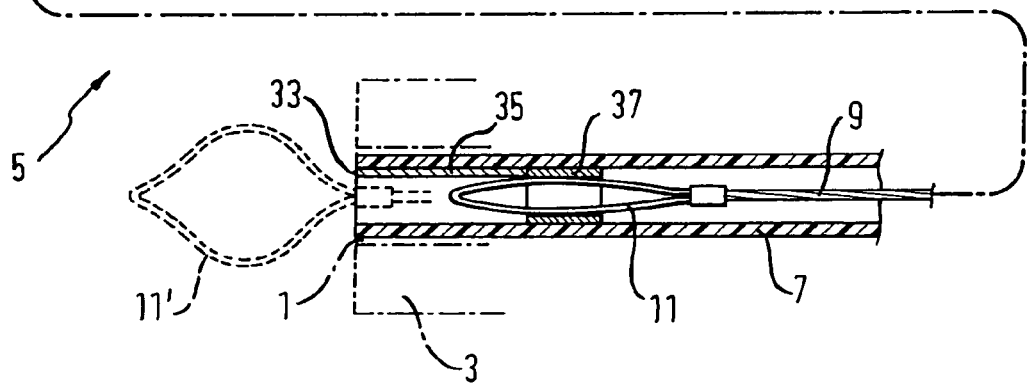
Fig. 6
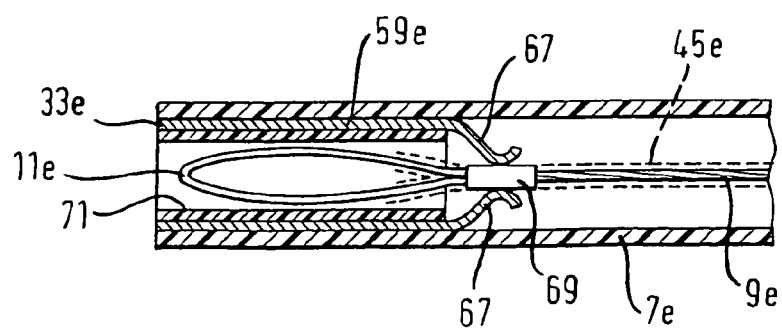

ELECTROSURGICAL INSTRUMENT FOR AN ENDOSCOPE OR A CATHETER

The invention relates to an electrosurgical instrument for an endoscope or a catheter.

It is known to coagulate and cut biological tissue with the aid of high-frequency electric currents. The current flows here between an active surgical electrode and a counter-electrode, or neutral electrode, which is applied in a fixed position onto a large surface area of the tissue. The surgical electrode can be applied directly to the tissue, so that coagulation or cutting can be performed in a targeted manner at a relatively low strength of the high-frequency current. Examples of electrosurgical electrodes of this kind are known from DE 32 47 793 C2 and DE 100 28 413 A1.

When coagulation is performed with contact surgical electrodes, it can happen that the electrode adheres to coagulated tissue, with the result that, when the electrode is removed, renewed bleeding, or even perforations of thin tissue structures, may occur. To perform coagulation of large areas of bleeding, it is known (DE 41 39 029 A1) to arrange the surgical electrode in the flow of an ionizable gas, for example argon, and to increase the high-frequency voltage on the electrode to such an extent that a plasma discharge from ionized gas is triggered between the surgical electrode and the tissue. Large areas of bleeding can be staunched without contact by means of this kind of plasma coagulation.

From U.S. Pat. No. 5,207,675, it is known to use one and the same surgical electrode both for contact coagulation and also for contactless plasma coagulation. In this known instrument, which can be introduced into an endoscope, the active surgical electrode can be pushed out of the instrument channel of the endoscope and lie free both for contact coagulation and also for plasma coagulation. However, since the high-frequency voltage for plasma coagulation has to be set considerably higher than for contact coagulation, undesired tissue reactions may occur if the surgical electrode touches the tissue during plasma coagulation.

To avoid these undesired tissue reactions, an arrangement is known from DE 197 31 931 A1 in which the surgical electrode lying free for contact coagulation, when pushed out from a flexible tube received by the instrument channel of the endoscope, is retracted completely into the tube so as to protect the tissue from direct contact by the electrode when the electrode is to be operated in plasma mode at increased high-frequency voltage. A sensor configured, for example, as a microcircuit switch or miniature light barrier, and arranged at the distal end of the tube, controls the high-frequency current generator and permits the plasma mode only when the electrode has been fully retracted. In order to control the high-frequency current generator, however, additional control lines running along the instrument channel of the endoscope are needed between the sensor at the distal end of the instrument and the high-frequency current generator connected to the proximal end of the instrument.

The object of the invention is to make available a comparatively simple electrosurgical instrument for an endoscope, which instrument can be used both in a contact coagulation or cutting mode and also in a non-contact plasma coagulation mode.

The invention starts out from an electrosurgical instrument for an endoscope, comprising a preferably flexible tube which can be introduced into an instrument channel of the endoscope, is electrically non-conductive at least on its outer face, and is open at its distal end, the proximal end of which tube can be connected to a gas source for ionizable gas, in particular argon, an electrode connection line which is longitudinally displaceable in the tube and whose proximal end can be connected to a high-frequency current generator, an electrosurgical electrode at the distal end of the electrode connection line, a handling device which is connected to the proximal end of the electrode connection line and by means of which the electrosurgical electrode, by way of the electrode connection line, can be pushed out of the distal end of the tube and can be drawn completely into the tube.

The improvement according to the invention is characterized in that a stationary electrode is arranged at the distal end of the tube and is stationary relative to this end, said stationary electrode being electrically conductively connected to a contact element which is arranged in the tube, at a distance from the distal end thereof, and which, when the electrosurgical electrode is drawn into the tube, is in electrical contact with the electrosurgical electrode and/or with the electrode connection line.

For the contact coagulation or cutting mode, the electrosurgical electrode is pushed out of the tube and is not in electrical contact with the stationary electrode or the contact element. For the plasma coagulation mode, it is drawn into the tube. Since, in the retracted position, the electrosurgical electrode or its connection line is reliably connected in an electrically conductive manner to the stationary electrode via the contact element, the plasma discharge is triggered and maintained by the stationary electrode. The stationary electrode is arranged safe from contact in the tube or is otherwise insulated so as to be safe from contact, such that, for example, contact burns during the plasma coagulation mode are avoided. The contact element is in this case dimensioned and arranged in such a way that the high-frequency current is delivered reliably to the stationary electrode only when the electrosurgical electrode, mounted displaceably in the tube, has been drawn sufficiently far back into the tube and its distal end is situated inside the tube. Therefore, the instrument according to the invention does not require any visual monitoring of the electrode retraction position via the optics system of the endoscope, which fact simplifies the use of the instrument.

The tube, which is expediently designed as an electrically insulating, flexible plastic hose, insulates both the retracted electrosurgical electrode and also the stationary electrode from the outside. In addition, the electrical connection between the active electrode surface of the stationary electrode and the contact element can be electrically insulated relative to the electrosurgical electrode; for example by an insulating material sleeve provided in the area axially between the active electrode surface of the stationary electrode and the contact element. Alternatively, or also in addition to this, the electrode connection line and/or the electrosurgical electrode can be provided at least partially with an insulation coating which is left open at a site overlapping the contact element in the fully retracted position. Thus, only in the fully retracted position is the contact element connected to the electrode connection line or electrosurgical electrode via the break in the insulation coating. The distal end of the tube expediently carries a sleeve made of heat-resistant, electrically insulating material, for example a ceramic sleeve, in order to ensure that the plastic hose is not heat-damaged by the plasma discharge.

In a preferred embodiment, the contact element is designed as a sleeve of electrically conductive material inserted into the tube. The sleeve can be a part of a metal wire coil or a part of a metal tube. In both variants, the stationary electrode can easily be made integral with the contact element, for example by the metal wire coil part being provided with an endpiece forming the stationary electrode and reaching to the distal end of the tube, or by the sleeve being lengthened as far as the distal end of the tube in order to form the stationary electrode. In the aforementioned embodiments, the sleeve is provided with an extension forming the stationary electrode. The extension can be formed integrally on the sleeve; however, the extension is preferably a separate conductor section, for example a wire section, which is applied conductively onto the sleeve, for example welded onto it. The materials of the sleeve and of the extension can thus be chosen independently of one another. Thus, the sleeve is preferably a metal tube section made of stainless steel, whereas the extension is a tungsten wire.

In the embodiments explained above, the contact element is formed by the sleeve. In one variant, the sleeve serves only as a support which holds the contact element at the distal end of the tube. Thus, the sleeve can carry an extension forming the stationary electrode and reaching almost to the distal end of the tube, which extension forms the contact element at an axial distance from the distal end of the tube. In the area of the distal end of the tube, the extension forming the stationary electrode can project, substantially central with respect to the tube toward the distal end of the latter and, in the area of the sleeve, can form the contact element. If the surgical electrode is designed as a flexible wire loop, then it can be pushed past the extension and out of the tube. When the wire loop is drawn back, the centrally arranged extension threads itself into the wire loop until the latter, in the fully retracted position, rests electrically conductively on the contact element. The contact element thus at the same time forms an end-stop for the retraction movement.

In one variant, however, the sleeve can also be provided with at least one radially resilient tongue forming the contact element and, if appropriate, can reach almost to the distal end of the tube and at the same time form the stationary electrode. The tongue can either be formed integrally on the sleeve or can be applied onto it, for example welded onto it.

To prevent contact when the electrosurgical electrode is still pushed forward, the continuation of the sleeve between an area at the distal end forming the stationary electrode and an area at the proximal end forming the contact element can be provided with an insulation. However, the insulation can in some cases be dispensed with if the handling device comprises abutment means which limit the movement of the electrosurgical electrode when it is in the position fully drawn into the tube. Such abutment means are also of advantage in other constructions of the stationary electrode or of the contact element since they mechanically signal to the operator that the electro-surgical electrode is sufficiently retracted.

The treatment parameters of the high-frequency generator can be switched manually (e.g. by means of foot pedals) between the high-frequency output required for contact treatment, with relatively low voltage, and the parameters required for plasma coagulation, with high voltage. However, the switching can also be done automatically if the handling device comprises sensor means, particularly in the from of a switch, which detect the fully retracted position of the electrosurgical electrode as a function of the position of the electrode connection line relative to the tube. In contrast to the sensor means known from DE 197 31 931 A1, the sensor means in this case can be provided at the proximal end of the tube, such that control lines running along the instrument channel of the endoscope are dispensed with.

The electrosurgical instrument according to the invention can be equipped, for contact coagulation or cutting, with any desired electrosurgical electrodes. Flexible wire loops are suitable, for example, or injection needles for sclerosing or the like. The electrosurgical electrode can have a bipolar structure for the contact coagulation mode, or it can be provided with an insulation coating that limits the active electrode surface and avoids undesired tissue contact, such as is described in DE 100 28 413 A1, for example.

Illustrative embodiments of the invention are explained in more detail below with reference to a drawing, in which:

FIG. 1 shows a partially cross-sectioned, schematic representation of an electrosurgical instrument with a loop electrode;

FIGS. 5 and 6 show cross-sectional representations of further variants of the distal area of the instrument from FIG. 1

Figure 2:
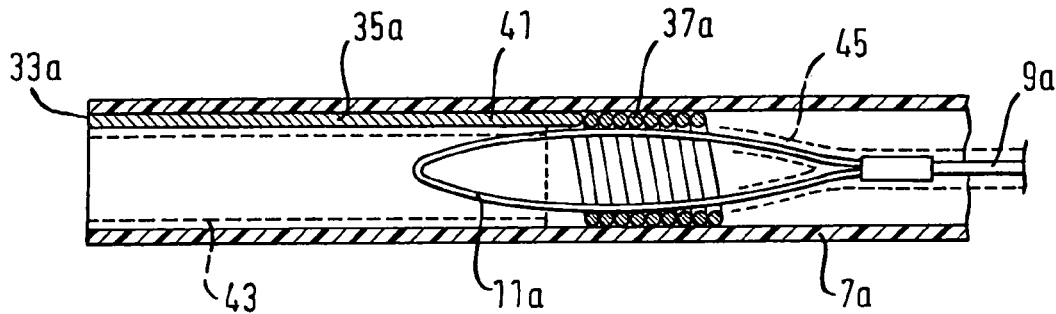
FIG. 2 shows a cross-sectional representation of the distal area in a variant of the instrument from FIG. 1.

FIG. 1 shows an electrosurgical instrument 5 which can be introduced into the instrument channel 1 of a flexible catheter, indicated by reference number 3, belonging to an endoscope, the rest of which is not shown in detail here. The instrument 5 has a closed-wall, flexible guide tube 7 which fits displaceably into the instrument channel 1 and is here in the form of a hose made of insulating plastic material in which a flexible connection line 9, for example in the form of a coiled cord, is in turn guided in a longitudinally displaceable manner. Provided at the distal end of the connection line 9 there is an electrosurgical electrode 11, here in the form of a resecting loop, which, with the aid of a handling device 13, can be pushed out of the distal end of the guide tube 7, as is indicated by 11', and can be completely retracted into the guide tube 7. In the completely retracted state, the electrode 11 is arranged at a distance from the distal end of the guide tube 7.

The handling device 13 has a shaft 15 which is connected to the proximal end of the guide tube 7 and along which it is possible to move a finger grip 17 which is connected securely to the proximal end of the connection line 9 to permit pulling and pushing thereof. To allow the handling device 13 to be operated with just one hand, the proximal end of the shaft 15 carries a thumb ring 19. An abutment 21 on the shaft 15 limits the displacement movement of the finger grip 17 in the completely retracted position of the electrode 11 shown in FIG. 1. By pushing the finger grip 17 forward into the position indicated by 17', the electrode 11 is pushed out from the distal end of the guide tube 7 via the connection line 9. The finger grip 17 carries a plug contact 23 which is connected to the proximal end of the connection line 9 and to which a high-frequency current generator 25 can be connected.

The electrode 11 arranged on the distal end of the connection line 9 permits contact coagulation and cutting of biological tissue under the action of the high-frequency current from the generator 25. The generator 25 comprises a counter-electrode of large surface area which bears on tissue that is not to be treated. The electrode 11 can have a completely exposed contact surface. However, electrodes which are provided partially with an insulating jacket and in which the insulating jacket reduces the active electrode surface, as is described for example in DE 100 28 413 A1, are also suitable. Bipolar electrodes are, however, also suitable if the connection line 9 has a two-core configuration.

The electrosurgical instrument 5 also permits operationally reliable plasma coagulation of large areas of tissue. For this purpose, the handling device 13 is provided with a gas attachment 27 through which ionizable gas, for example argon, can be delivered from a gas source 29 at the proximal end of the guide tube 7. As is indicated at 31, the proximal end of the guide tube 7 is sealed off so that the gas escapes from the distal end of the guide tube 7. At the distal end, a stationary electrode 33 for the tissue that is to be coagulated is arranged safe from contact in the guide tube 7, this stationary electrode 33 being electrically connected to a contact sleeve 37 via a connection area 35. When the electrode 11 is in the fully retracted position, it bears resiliently on the inner circumference of the contact sleeve 37 and connects the stationary electrode 33 electrically conductively to the connection line 9.

For plasma coagulation, the finger grip 17 is drawn back as far as the abutment 21. It is thus ensured that the electrode 11 designed for contact coagulation is retracted completely into the distal end of the guide tube 7 without this requiring visual control via the optics system of the endoscope. The gas source 29 and the high-frequency current generator 25 are then switched on, the current strength of the generator 25 being increased, if appropriate manually, to a value sufficient for initiating a plasma discharge in the gas stream emerging at the distal end of the guide tube 7. For switching the high-frequency voltage of the generator from the low value, required for contact treatment by means of the electrode 11, to the higher value required for the plasma coagulation, a two-pedal foot switch can be used. However, it is also possible to provide a switch mechanism 39 on the handling device 13, for example in the area of the abutment 21, which switch mechanism allows the switching of the generator 25 to be controlled either automatically or manually.

In the illustrative embodiment shown, the guide tube 7 is designed overall as a nonconductive hose. It will be appreciated that the guide tube can also be designed as a coil spring with an outer insulating jacket, provided that the contact sleeve 37, the connection area 35 and the stationary electrode 33 are insulated relative to the metal coil spring. If the reverse movement of the finger grip 17, as indicated in FIG. 1, is limited by an abutment 21 which defines the fully retracted position of the electrode 11, then the stationary electrode 33, the connection area 35 and also the electrode 11 can be uninsulated, because the generator 25 is switched to the parameters required for plasma coagulation only when it is in the position defined by the abutment 21.

The connection area 35, forming at its end the stationary electrode 33, is designed as an elongate extension projecting from the contact sleeve 37. The contact sleeve 37 is expediently a metal tube section, for example of stainless steel, on which the extension can be integrally formed. However, the extension is preferably a wire section which is applied conductively onto the contact sleeve, for example soldered onto it or welded onto it, preferably a tungsten wire section.

Variants of the electrosurgical element are described below. Components with the same function are provided with the reference numbers from FIG. 1 and, in order to differentiate them, with a letter. To explain the structure and mode of action, including of possible variants, reference is made to the description of FIG. 1 and also to the following description. The variants explained below concern embodiments of the distal end of the instrument.

In the embodiment in FIG. 2, the electrosurgical electrode 11a connected to the distal end of the connection line 9a is again designed as a flexible loop electrode automatically spreading open outside the guide tube 7a, similarly to FIG. 1. The guide tube 7a is once again a flexible plastic hose. The contact sleeve 37a is designed as part of an elastic metal wire coil onto which an endpiece 41, configured as a leg spring and protruding rectilinearly along the guide tube 7a, is integrally connected in order to form the electrode 33a and connection area 35a reaching to the distal end of the guide tube 7a. To avoid electrical contact between the electrode 11a, outside its retracted position shown in FIG. 2, and the stationary electrode 33a or connection area 35a, an insulating jacket indicated at 43, for example in the form of a plastic hose section, can be inserted into that area of the distal end of the guide tube 7a axially covered by the electrode 33a and the connection area 35a. In addition, or alternatively, that area of the electrode 11a oriented toward the proximal end, in the completely retracted position of the electrode 11a, including the connection line 9a, can be surrounded by a jacket of insulating material, as indicated at 45. It suffices if the jacket 45 extends along the axial length of the electrode 33a, the connection area 35a and the contact sleeve 37a.

Figure 3:
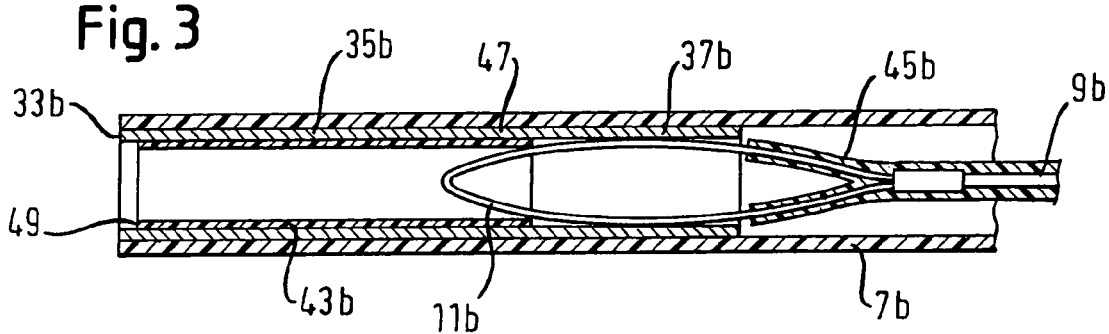
FIG. 3 shows a cross-sectional representation of a further variant of the distal area of the instrument from FIG. 1.

In the illustrative embodiment in FIG. 3, the electrosurgical electrode 11b connected to the distal end of the connection line 9b is once again designed as a loop electrode. A metal sleeve 47 is inserted into the distal end of the guide tube 7b and ends flush with said distal end of the guide tube 7b, which metal sleeve 47 forms the contact sleeve 37b in the area of its proximal end, the stationary electrode 33b at its distal end, and, integrally between these, the connection area 35b. The sleeve 47 can be a part of a rigid metal tube or of a flexible wire coil. As has been explained in connection with FIG. 2, the inner jacket of the metal sleeve 47 can be lined with an insulation coating 43b, for example in the form of a plastic tube section, but this expediently ends at a distance from the distal end of the guide tube 7b in order to increase the active surface area of the stationary electrode 33b, as is indicated by 49 in FIG. 3. That area of the electrode 11b and of the connection line 9b oriented toward the proximal end is surrounded by a jacket of insulating material 45b, as in FIG. 2. The insulations 43b and 45b can, if appropriate, be omitted.

Figure 4:
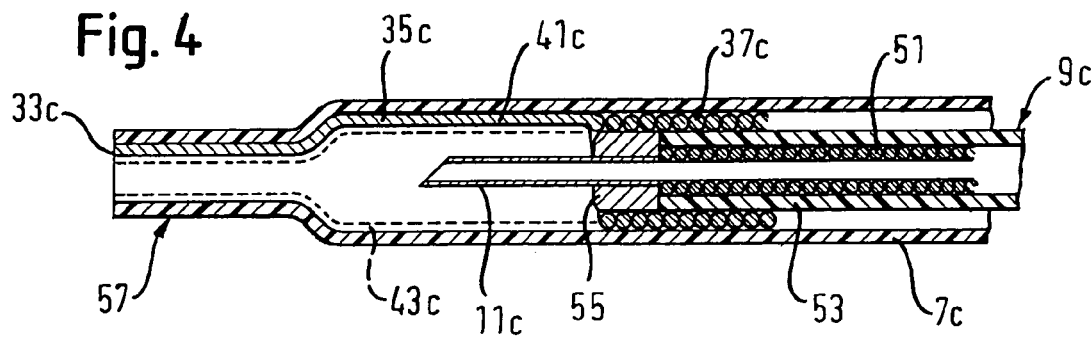
FIG. 4 shows a cross-sectional representation of the distal area of a variant of the instrument, with a sclerosing needle as electrosurgical electrode.

In the variant of the instrument according to FIG. 4, the electrosurgical electrode 11c is designed, for example for sclerosing purposes, as an injection needle which is connected via a tubular connection line 9c to the handling device. Treatment fluid can be delivered, in a manner not shown, to the proximal end of the tubular connection line 9c. The connection line 9c comprises a metal wire coil 51 whose outer jacket is surrounded by a plastic hose 53. The metal wire coil 51 ends on a metal head 55 which holds the metal injection needle of the electrode 11c and which, when the electrode 11c is fully retracted into the guide tube 7c, touches the contact sleeve 37c, which is here designed as part of a wire coil. Similarly to the variant in FIG. 2, the wire coil 37 is provided integrally with a leg 41c whose distal end forms the stationary electrode 33c and connects it to the contact sleeve 37c via the connection area 35c.

The guide tube 7c, between the contact sleeve 37c and its distal end, is narrowed to form a guide section 57 for centering and guiding the electrode 11c. In the variant in FIG. 4 too, the area between the electrode 33c and the contact sleeve 37c can be provided with an insulation 43c.

To be able to deliver the treatment fluid from the handling device, the proximal end of the hose 53 is provided with an attachment piece which at the same time is also in electrical contact with the wire coil 51, that is to say at the same time assumes the function of the plug contact 23 from FIG. 1. In this way, it is possible to avoid inadvertent contact of the treatment fluid attachment during coagulation. It will be appreciated that, instead of the wire coil 51, the connection line 9c can also be designed as a separate cord or the like inside or outside of the hose 53. The wire coil 51 can also enclose the hose 53 from the outside.

Figure 5:
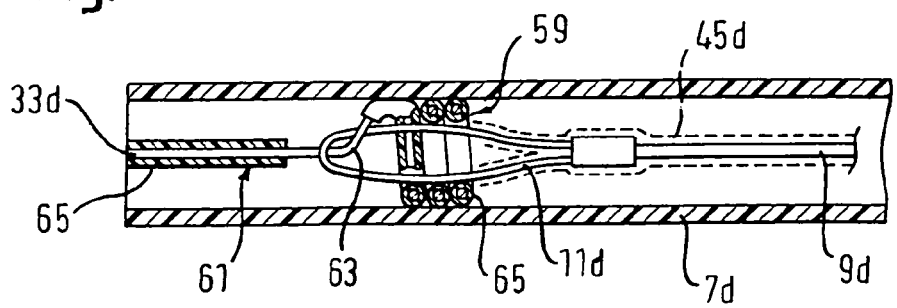

In the embodiments of the electrosurgical instrument explained above, the contact sleeve inserted into the guide tube provides for the electrical contact with the electrosurgical electrode. FIG. 5 shows a variant in which a sleeve 59, here designed as a coil spring section, is inserted into the guide tube 7d, which is once again designed as a plastic hose. The sleeve 59 serves as a carrier for an extension 61 which extends approximately centrally in the guide tube 7d to its distal end and which, at the distal end of the guide tube 7d, forms the stationary electrode 33d. In the embodiment shown, the extension 61 is an endpiece projecting from the coil spring section forming the sleeve 59. Except for an exposed contact area 63 where the axially extending extension 61 merges into the coil spring section, the extension 61 made of metal wire, for example tungsten wire, including the coil spring section of the sleeve 59, has an electrical insulation 65.

The electrosurgical electrode 11d is designed as a flexible resecting loop and, including its connection line 9d displaceable in the guide tube 7d, can be provided in a manner known per se with an electrical insulation 45d. The resecting loop 11d can be pushed past the extension 61d and out of the guide tube 7d for contact coagulation and cutting of biological tissue. Since the extension 61 forming the stationary electrode 33d is arranged centrally in the guide tube 7d, the extension 61 threads onto the extension 61 when the resecting loop 11d is drawn back in, until the resecting loop 11d, in the fully retracted position, rests on the contact area 63 for the plasma coagulation mode.

It will be appreciated that the sleeve 59 can also be designed as a metal tube section. Furthermore, the extension 61 can be formed integrally on the metal tube. However, the extension 61 can also be designed as a wire section which is applied conductively onto the metal tube section, for example welded onto it. If appropriate, the metal tube section can have an insulation coating on its inner face.

In the embodiment in FIG. 6 also, the sleeve 59e designed as a metal tube section serves as a carrier for radially elastic contact spring tongues which project from the proximal end of the sleeve 59e and which, when the electrosurgical electrode 11e is in the retracted position, make electrically conductive contact with the connection line 9e, in this case with the latter's bushing 69 which connects the electro-surgical electrode 11e to the connection line 9e.

The sleeve 59e extends to the distal end of the guide tube 7e and at the same time forms the stationary electrode 33e there. Except for the contact spring tongues 67, the inner circumference of the sleeve 59e is lined with an insulation coating 71. The electrosurgical electrode 11e, designed as a resecting loop in the illustrative embodiment shown, and the connection line 9e are likewise provided with an electrically insulating coating 45e, which only leaves open the contact area of the bushing 69.

In the illustrative embodiment shown, the contact spring tongues 67 are formed integrally on the sleeve 59e. It will be appreciated that the contact spring tongues can, if appropriate, also be designed separate from the sleeve 59e. For example, the sleeve 59e as a whole can be made of plastic material, while the contact spring tongues 67 are connected to axially extending extensions forming the stationary electrode and are fixed in the sleeve.

The invention claimed is:

1. An electrosurgical instrument for an endoscope or a catheter, comprising:
   a) a preferably flexible tube which can be introduced through an instrument channel of the endoscope or through a catheter lumen, is electrically nonconductive at least on its outer face, and is open at its distal end, the proximal end of which tube can be connected to a gas source for ionizable gas, in particular argon;
   b) an electrode connection line which is longitudinally displaceable in the tube and whose proximal end can be connected to a high-frequency current generator;
   c) an electrosurgical electrode at the distal end of the electrode connection line; and
   d) a handling device which is connected to the proximal end of the electrode connection line and by means of which the electrosurgical electrode, by way of the electrode connection line, can be pushed out of the distal end of the tube and can be drawn into the tube, wherein a stationary electrode is arranged at the distal end of the tube and is stationary relative to this end, said stationary electrode being electrically conductively connected to a contact element which is arranged in the tube, and which, when the electrosurgical electrode is drawn into the tube, is in electrical contact with the electrosurgical electrode and/or with the distal end of the electrode connection line.

2. The electrosurgical instrument as claimed in claim 1, wherein the tube is designed as an electrically insulating, flexible plastic hose.

3. The electrosurgical instrument as claimed in claim 1, wherein the electrical connection between the active electrode surface of the stationary electrode and the contact element is electrically insulated relative to the electrosurgical electrode.

4. The electrosurgical instrument as claimed in claim 3, wherein an insulating material sleeve is provided in the area axially between the active electrode surface of the stationary electrode and the contact element and covers the electrical connection.

5. The electrosurgical instrument as claimed in claim 1, wherein the electrode connection line and/or the electrosurgical electrode are provided at least partially with an insulation coating which ends or is left open at a site overlapping the contact element in the retracted position.

6. The electrosurgical instrument as claimed in claim 1, wherein the contact element is designed as a sleeve of electrically conductive material inserted into the tube.

7. The electrosurgical instrument as claimed in claim 6, wherein the sleeve is provided with an extension forming the stationary electrode and reaching almost to the distal end of the tube.

8. The electrosurgical instrument as claimed in claim 6, wherein the sleeve is designed as part of a metal tube.

9. The electrosurgical instrument as claimed in claim 6, wherein the sleeve is designed as part of a metal wire coil.

10. The electrosurgical instrument as claimed in claim 9, wherein the metal wire coil part is provided with an endpiece forming the stationary electrode, reaching almost to the distal end of the tube, and forming the extension.

11. The electrosurgical instrument as claimed in claim 6, wherein an insulating material sleeve, which encloses at least part of the extension between itself and the tube, is inserted into the tube.

12. The electrosurgical instrument as claimed in claim 6, wherein the sleeve reaches almost to the distal end of the tube and at the same time forms the stationary electrode.

13. The electrosurgical instrument as claimed in claim 12, wherein the inner jacket of the sleeve carries an insulating material layer between an area at the distal end forming the stationary electrode and an area at the proximal end forming the contact element.

14. The electrosurgical instrument as claimed in claim 6, wherein the contact element is held on a sleeve inserted into the tube.

15. The electrosurgical instrument as claimed in claim 14, wherein the sleeve carries an extension forming the stationary electrode and reaching almost to the distal end of the tube, which extension forms the contact element at an axial distance from the distal end of the tube.

16. The electrosurgical instrument as claimed in claim 15, wherein the extension, in the area of the distal end of the tube, projects substantially central with respect to the tube, toward the distal end of the latter and, in the area of the sleeve, forms the contact element, and wherein the electrosurgical electrode is designed as a flexible wire loop.

17. The electrosurgical instrument as claimed in claim 14, wherein the sleeve reaches almost to the distal end of the tube and at the same time forms the stationary electrode, and wherein the sleeve carries at least one radially resilient tongue forming the contact element.

18. The electrosurgical instrument as claimed in claim 1, wherein the handling device comprises abutment means which limit the movement of the electrosurgical electrode in the proximal direction when it is in the position drawn into the tube.

19. The electrosurgical instrument as claimed in claim 1, wherein the handling device comprises sensor means, particularly in the form of a switch, which detect the retracted position of the electrosurgical electrode as a function of the position of the electrode connection line relative to the tube.

20. The electrosurgical instrument as claimed in claim 1, wherein the electrosurgical electrode is designed as a flexible wire loop.

21. The electrosurgical instrument as claimed in claim 1, wherein the electrosurgical electrode is designed as an injection needle, which is connected to the handling device via a hose which is displaceable in the tube.

22. The electrosurgical instrument as claimed in claim 1, wherein the contact element is arranged in the tube at a distance from the distal end thereof.

* * * * *